United States Patent [19]
Terhune

[11] Patent Number: 5,492,012
[45] Date of Patent: Feb. 20, 1996

[54] TIME-OF-FLIGHT METHOD FOR SIZING CRACKS THROUGH FLUID-FILLED GAPS IN STRUCTURES

[75] Inventor: James H. Terhune, San Jose, Calif.

[73] Assignee: General Electric Company, San Jose, Calif.

[21] Appl. No.: 966,492

[22] Filed: Oct. 26, 1992

[51] Int. Cl.⁶ ................................................ G01N 29/00
[52] U.S. Cl. ................................................ 73/598; 73/596
[58] Field of Search ........................ 73/598, 596, 597, 73/628, 624

[56] References Cited

U.S. PATENT DOCUMENTS

| | | | |
|---|---|---|---|
| 4,522,064 | 6/1985 | McMillan | 73/628 |
| 4,570,487 | 2/1986 | Gruber | 73/628 |
| 4,658,649 | 4/1987 | Brook | 73/598 |
| 5,118,464 | 6/1992 | Richardson et al. | 376/252 |

FOREIGN PATENT DOCUMENTS

| | | |
|---|---|---|
| 0289383 | 11/1988 | European Pat. Off. . |
| 0503977 | 9/1992 | European Pat. Off. . |
| 2121964 | 1/1984 | United Kingdom . |

OTHER PUBLICATIONS

Locating and Sizing Surface-breaking Cracks, by Peterson et al., *Materials Evaluation*, 42, Apr. '84.
J. P. Charlesworth et al., Engineering Applications of Ultrasonic Time-of-Flight Diffraction, John Wiley & Sons, Inc., 1989, pp. 1–34.

J. & H. Krautkramer, Ultrasonic Testing of Materials, Springer-Verlag, 4th Ed., 1990, pp. 18–23.

Primary Examiner—Richard E. Chilcot, Jr.
Assistant Examiner—R. Biegel
Attorney, Agent, or Firm—James E. McGinness

[57] ABSTRACT

A method and apparatus for sizing a surface-connected planar crack through a gas- or liquid-filled gap. Ultrasonic energy having a frequency equal to the resonant frequency of the gap is emitted toward the crack edge. A first portion of the energy is back-scattered by the crack edge toward the emitter in a detection mode and a second portion is scattered by the crack edge toward a surface to which the crack is connected, which reflects the second portion toward a detector. The difference between the respective times-of-flight from emission to detection of the first and second portions is measured and used to determine the depth of penetration of the surface-connected crack. The paths traveled by the first and second portions of said emitted ultrasonic energy substantially intersect at the gap. A similar method also applies in sizing buried planar cracks across fluid-filled gaps.

6 Claims, 5 Drawing Sheets

TIME-OF-FLIGHT METHOD FOR SIZING CRACKS THROUGH FLUID-FILLED GAPS IN STRUCTURES

FIELD OF THE INVENTION

This invention relates generally to non-destructive examination of material, such as metal, for voids, flaws, cracks and other defects that can be detrimental to the integrity of the material. Specifically, the invention relates to the ultrasonic inspection of nuclear and non-nuclear components at operating plants and facilities.

BACKGROUND OF THE INVENTION

Ultrasonic characterization of cracks in materials is at least a two-step process: 1) detection and location; and 2) sizing in absolute or relative terms.

U.S. Pat. No. 5,118,464 discloses a method for detecting the presence of material flaws, such as a crack 8 (see FIG. 1 herein), behind normally opaque barriers, such as fluid-filled gap 6 between structures 2 and 4. In this method transducer 10 is excited to emit a longitudinal ultrasonic wave which is coupled to structure 2 via couplant 12, e.g., normal water in a nuclear reactor. At the correct frequency the emitted wave bridges the gap and enters structure 4, where it is reflected by crack 8. The return path of the reflected wave also bridges the gap and the wave impinges on the transducer 10, where it is detected as a "pulse echo" signal.

However, the determination of the crack size, or depth of penetration in the case of surface-connected flaws, is a different and more complicated task. Because of the special constraints placed on the system by the presence of the fluid-filled gap, novel means are required to determine the crack size.

A conventional method for determining the depth of penetration of a planar crack 8', known as the time-of-flight diffraction technique, is illustrated in FIG. 2. This method takes advantage of the forward scattering of waves of ultrasonic energy at the edge 24 of crack 8' connected to back surface 18 of wall 14. An emitter of short pulses of ultrasound, coupled to the inspection surface 16 at location 20 which is a distance S from the plane 26 of the crack (or its vertical projection), causes refracted sound waves 22 to impinge on the crack edge 24, which scatters the ultrasonic energy in all directions. A detector situated at location 30, a distance S on the opposite side of the crack plane 26, is excited by the ray 28 of scattered pulsed energy after a time delay that is a function of S, the crack height h, and the known wall thickness $D_w$.

In accordance with this method, the two legs of the detection triangle need not be equal in length, but the geometry is simpler for this case, and the same type of transducer can be used for emission and detection. Either shear or longitudinal waves may be used, depending on the type of transducer employed.

By measuring the time-of-flight of the pulses from the emitter to the detector by way of the crack edge, the crack height h can be easily computed from the geometry of FIG. 2 (although the time-of-flight does not determine the details of crack orientation, or aspect).

Inspection methods using the ultrasonic time-of-flight diffraction technique have been devised for buried, as well as surface-connected, cracks and have proven to be the most accurate means of crack sizing in practice. Corrections for surface curvature effects can be employed for use with pipes and nozzles, where necessary, to enhance accuracy. On the other hand, the method clearly fails if the scattered wave is unable to reach the detector, which occurs if there is a relatively non-uniform gap interposed between the inspection surface 16 and the crack edge 24.

Detection and sizing of cracks behind machined gaps are required for inspection of certain structures in nuclear power plants. These gaps are present by design and usually are not entirely uniform, because of dimensional tolerances and variations in positioning and joining. In cases of interest, the gap may have water or helium gas injected to assure that the resonant frequency is consistent with ultrasonic frequencies commonly used for detection and sizing of material cracks. However, for non-uniform gaps, the gap transmission frequency varies along the gap and is a weak function of the angle-of-incidence at the gap surface, as will be shown below. This makes the standard time-of-flight method inapplicable, since little scattered energy reaches the detector location shown in FIG. 2.

SUMMARY OF THE INVENTION

The present invention overcomes the aforementioned disadvantage of the conventional time-of-flight diffraction technique by providing a method for accurately sizing cracks which lie behind a gap filled with water or gas. The time-of-flight from emitter to crack edge and back to the detector is a function of the crack height and the geometric parameters. The time-of-flight data can be used to determine the height of both surface-connected and buried planar cracks.

The invention utilizes the principle of constructive interference to form a standing wave in the medium which fills the gap. The ultrasonic wave generated by the emitter is a wave packet having a length at least twice the width of the gap to be bridged and a frequency selected to ensure the creation of a constructively interfering standing wave in the gap. The wave of the standing wavelength is half the width of the gap to be bridged.

In accordance with the method and apparatus of the invention, the emitter and detector are positioned in proximity to each other, on one side of the plane of a crack which has already been detected. The transducers are positioned such that the incident ray and the reflected ray cross the intervening gap at the same point, so that the gap transmission frequencies for the incident and reflected rays will be the same. Proper selection of the frequency of the emitted wave packet will ensure that the incident and reflected rays are substantially transmitted across the gap.

The apparatus for carrying out the method of the invention includes means for supporting the emitter and detector in a manner that allows slidable adjustment of their relative positions along an axis. In particular, the apparatus includes a sled with tracks on which transducer dollies slide, means for adjusting the distance between the emitter and detector and means for encoding the emitter location.

The method and apparatus of the invention provide a unique means of accurately sizing flaws behind normally opaque, non-uniform gaps. The method utilizes back-scattered time-of-flight data in a deterministic way to accurately and uniquely size cracks. The method is based on a novel sizing algorithm relating the geometry, frequency, bandwidth and pulse time-of-flight to the interpretation of pulse time delays in terms of scattering from the extremity of a crack. The ultrasonic transducers are remotely and accurately positioned so as to optimize the acquisition and interpretation of pulse time-of-flight data radiating from a crack edge, whose location defines the normal projection of the crack height.

BRIEF DESCRIPTION OF THE DRAWINGS

The method and apparatus of the invention will be described in detail with reference to the drawings, wherein.

DETAILED DESCRIPTION OF THE PREFERRED EMBODIMENTS

Figure 3:
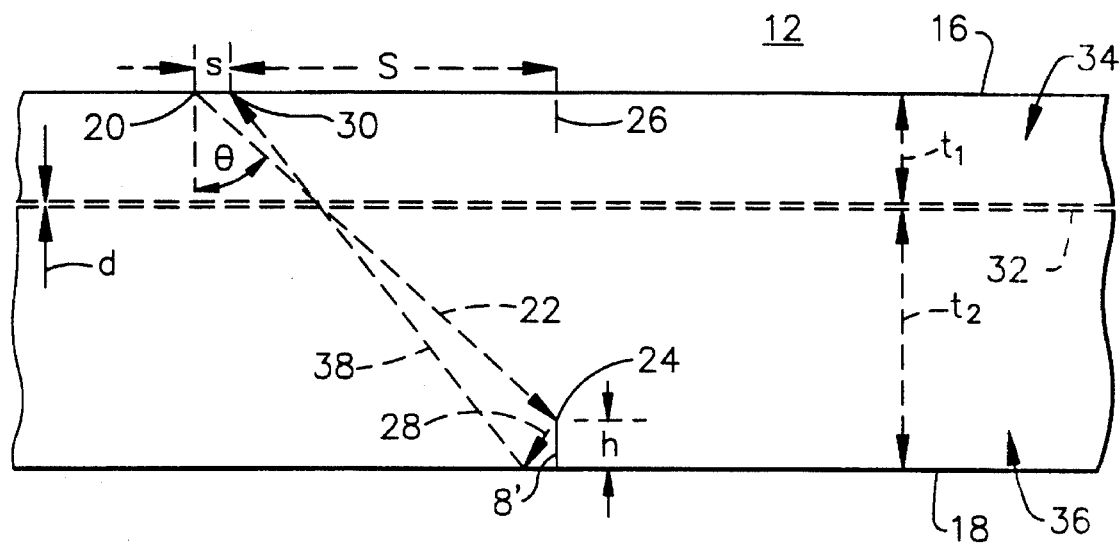
FIG. 3 is a schematic representation of a time-of-flight technique for sizing surface-connected cracks through fluid-filled gaps in accordance with the invention.

The time-of-flight method for sizing a surface-connected crack 8' across a fluid-filled gap 32 in accordance with the invention is depicted in FIG. 3. The crack 8' extends from the back surface 18 of wall 36 to crack edge 24.

As seen in FIG. 3, gap 32 of width d separates an inner wall 34 of thickness $t_1$ from an outer wall 36 of thickness $t_2$. Gap 32 is opaque to ultrasound, except for resonant frequencies for standing waves in the gap, as described in U.S. Pat. No. 5,118,464. Therefore, if the emitter at location 20 and the detector at location 30 are separated by a distance s which is of the order of the crack height h, the resonance condition in the gap is much more likely to occur than if the two transducers are separated by the distance 2S, which is of the order of $(t_1+t_2)$. The detector and emitter are located at respective distances S and (S+s) from the known crack plane 26. The emitter and detector could be reversed with respect to the crack plane, and/or with respect to each other, without changing the basic principle of operation and without departing from the scope of the invention.

The emitter at location 20 is coupled to inner surface 16 by surrounding water 12. The emitted ultrasonic waves enter inner wall 34 at an angle of refraction θ which is determined by the type of metal making up wall 34 and the type of transducer employed. For sizing surface-connected cracks, the emitter is of the focused type. The angle θ may be assumed to be a known value for the transducer mode of operation. For the sake of definiteness, the preferred longitudinal-wave mode is described, although similar considerations apply to shear waves.

The effective width $D_w$ of the wall is a function of the relative index of refraction n of the fluid, which in turn is a function of the fluid temperature $T_g$, and the angle of incidence θ, as well as the respective velocities of sound in the fluid at 0° C., $c_g$, and in the wall material, $c_s$. The fundamental resonant frequency $f_0$ in the gap is then determined by $D_w$ and $c_g$. These parameters are related by the following formulae:

$$D_w = t_1 + t_2 + d/n$$

$$n = \frac{c_g}{c_s} \sqrt{\left(1 + \frac{T_g}{273}\right)\left[1 - \left\{\frac{c_g}{c_s} \sin(\theta)\right\}^2\right]}$$

$$f_0 = \frac{c_g}{2d} \sqrt{\left(1 + \frac{T_g}{273}\right)\left[1 - \left\{\frac{c_g}{c_s} \sin(\theta)\right\}^2\right]}$$

The equations for n and $f_0$ are for an ideal gas; similar expressions hold for liquids.

Frequency $f_0$ depends on both θ and d, so scattered energy incident on the gap at angles other than θ will be reflected and go undetected. Furthermore, if d varies and is substantially different at the respective points where the incident and scattered energy impinge on the gap, reflection of the scattered energy at the gap will also occur. But the dependence on θ is very weak because numerically:

$$\left[\frac{c_g \sin[\theta]}{c_s}\right]^2 \ll 1$$

Figure 1:
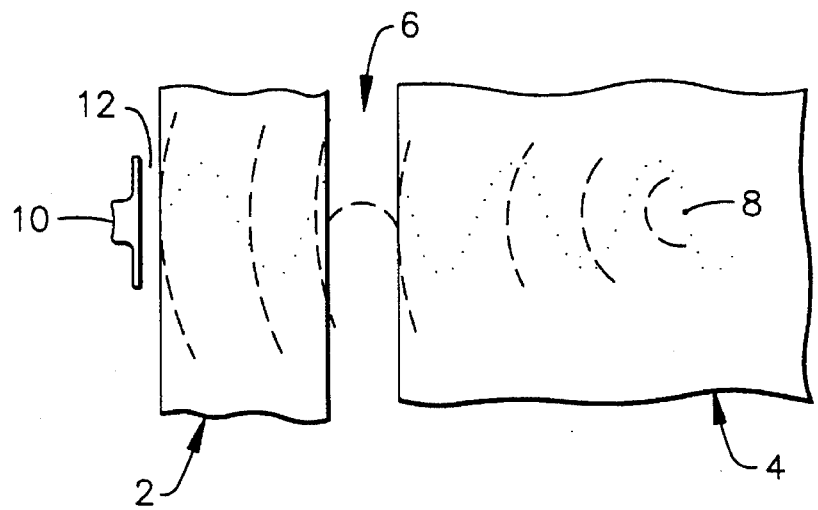
FIG. 1 is a schematic representation of conventional ultrasound interrogation of two structures separated by a gap.
Figure 2:
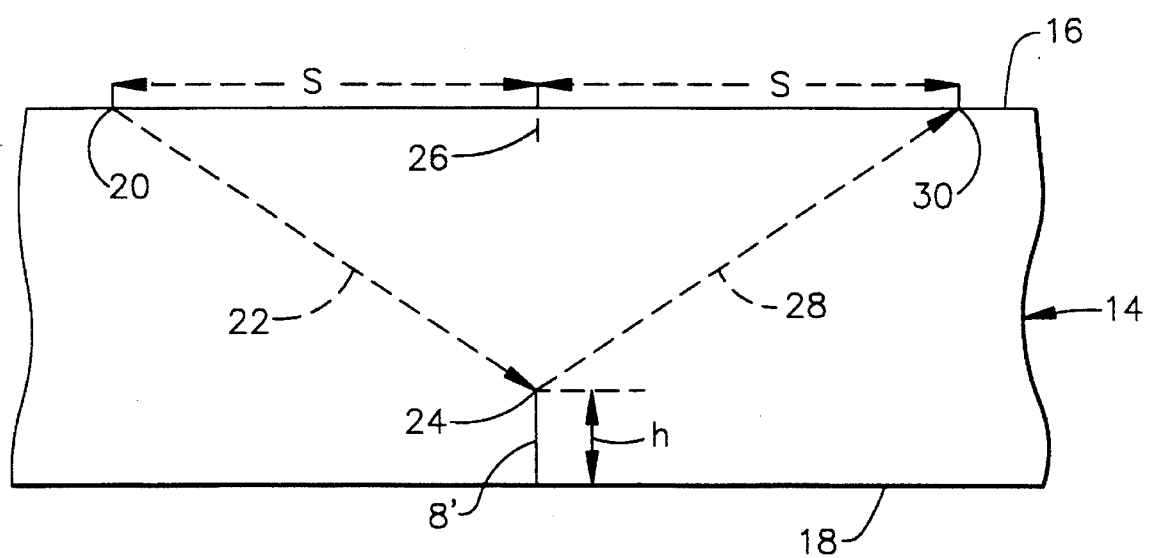
FIG. 2 is a schematic representation of a conventional time-of-flight diffraction technique used in sizing cracks.

Therefore, the main variable is gap width d, which in accordance with the method of the invention is the same for the incident and reflected rays of interest. This is ensured by the fact that paths 22 and 38 impinge on the gap 32 at a common point. In addition, the paths 22 and 38 lie fairly close together, thereby traversing the gap at nearly the same angle θ. Hence, the sizing geometry of FIG. 3 is preferred over that of FIG. 2, and the ultrasonic energy scattered by crack edge 24 can be used to determine crack height h.

This is accomplished by determining the difference ΔT between the time-of-flight of a ray incident along path 22 and scattered back along path 22 by crack edge 24 to the emitter at location 20 and the time-of-flight of a ray incident along path 22, scattered along path 28 by crack edge 24 and then reflected by back wall 18 along path 38 to a detector at location 30. The emitter is switched to a detection mode prior to the time of arrival of the ray scattered back along path 22.

The time-of-flight T is a complicated function of crack height and the geometric parameters. An exact equation can be derived relating these factors, which is fourth-order in h. To simplify deducing the value of h from the time data, an approximate expression is useful. Defining the parameters A, B, C and $d_w$ by:

$$A = -(4D_w)^2 + (2c_s \Delta T)^2 + \frac{32 d_w D_w \left(\frac{S}{D_w}\right)^2}{\left(1 - \frac{d_w}{D_w}\right)} + \frac{8\left(\frac{c_s \Delta T S d_w}{D_w^2}\right)^2 - \left[4 d_w \left(\frac{S}{D_w}\right)^2\right]^2}{\left(1 - \frac{d_w}{D_w}\right)^2}$$

-continued $$B = 8d_w \frac{\left(\frac{c_s \Delta TS}{D_w}\right)^2}{\left(1 - \frac{d_w}{D_w}\right)};$$

$$C = (2c_s \Delta T D_w)^2 + (2c_s \Delta TS)^2 - (c_s \Delta T)^4$$

results in a solution, good to second-order in $h/D_w$, which can be written symbolically as:

$$h \cong -\left(\frac{B}{2A}\right) + \sqrt{\left(\frac{B}{2A}\right)^2 - \frac{C}{A}}$$

This complicated formula can be further approximated by:

$$\frac{h}{D_w} \approx \frac{2}{9}\left(-1 + \sqrt{1 + \left(\frac{D_w}{t_1 + d/2n} - 1\right)\left[\left(\frac{c_s \Delta T}{2D_w}\right)^2 - \left(1 + \frac{S^2}{D_w^2}\right)\right]\left(\frac{9D_w^2}{2S^2}\right)}\right)$$

Figure 4:
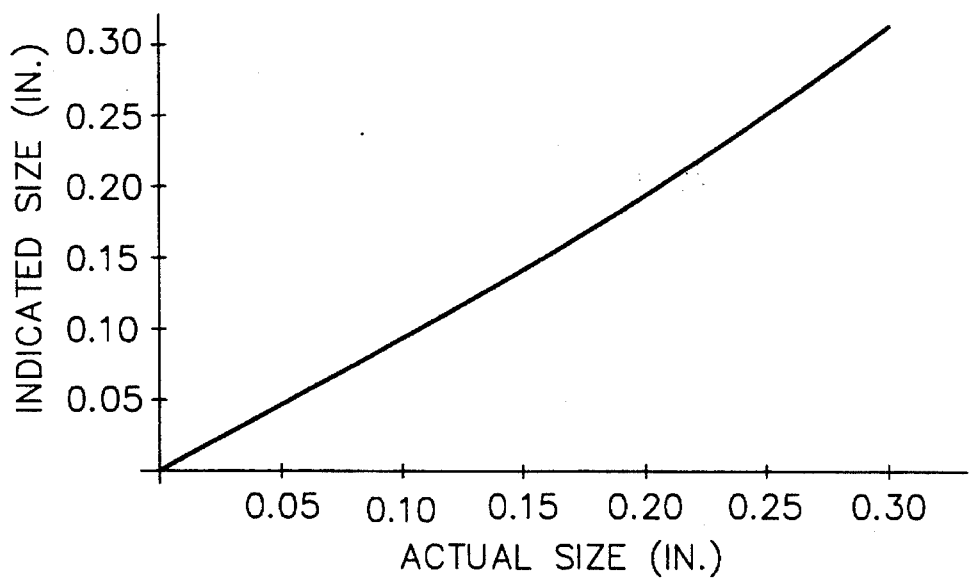
FIG. 4 is a graph depicting the accuracy of the sizing algorithm used in the method of the invention.

The accuracy of this expression is shown in FIG. 4 for a typical case. The curve is almost a straight line, indicating the approximate formula is accurate to within a few percent, even for relatively large cracks.

Note that the sizing algorithm is independent of s, which is only involved in obtaining a scattered signal, whose time delay is $\Delta T$. Thus, S and s are chosen so that a diffraction signal is received using transducers of refracted angle $\theta$ (72° longitudinal waves in this example). This is done by choosing S, assuming initially that the crack height h is a small fraction of $D_w$. Then, the emitter location 20 is determined by:

$$\frac{S}{D_w} \approx \tan[\theta]$$

The detector location 30 is selected by adjusting the distance between the transducers until a diffracted signal is received with the approximate time-of-flight:

$$T \approx \frac{2S}{c_s \sin[\theta]}$$

The initial values of S and s, thus obtained, are adjusted until a sufficiently strong diffraction signal is received, thereby optimizing the sizing geometry. Since both S and s depend on h, the optimum arrangement for a typical case is depicted in FIG. 5.

Figure 5:
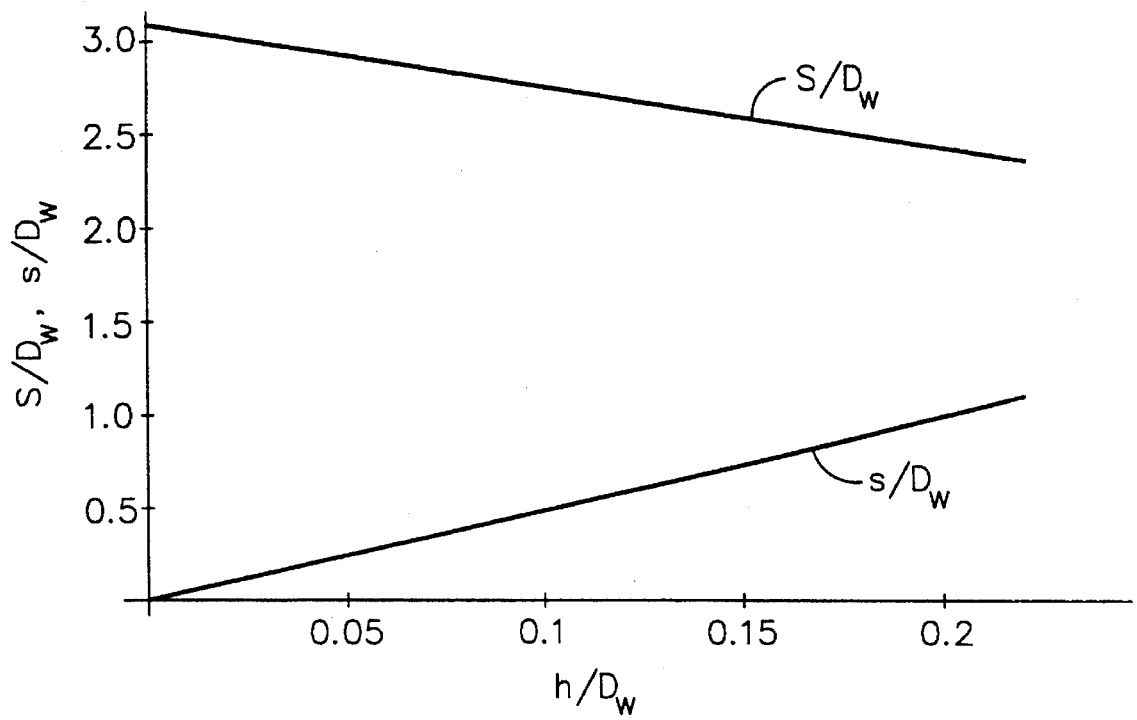
FIG. 5 is a graph depicting the dependence of the transducer coordinates on crack size in accordance with the method of the invention.

When the spacings satisfy the relationship shown in FIG. 5, the time-of-flight signal emitted at 20 and received at 30 can be measured accurately. The crack height h, normalized by $D_w$, is then calculated using the sizing equation with known geometrical factors. Similar curves can be obtained for any reasonable combination of the parameters shown in FIG. 5.

In accordance with the conventional time-of-flight diffraction technique, the distance s between transducers need not be variable. In fact, the distance s=2S is chosen irrespective of the crack size. This approach is not possible in the circumstance of an intervening gap, which is relatively non-uniform over the dimension 2S. Both S and s must be adjustable by remote means, in order to obtain the time-of-flight data required for sizing across the gap.

Figure 6A:
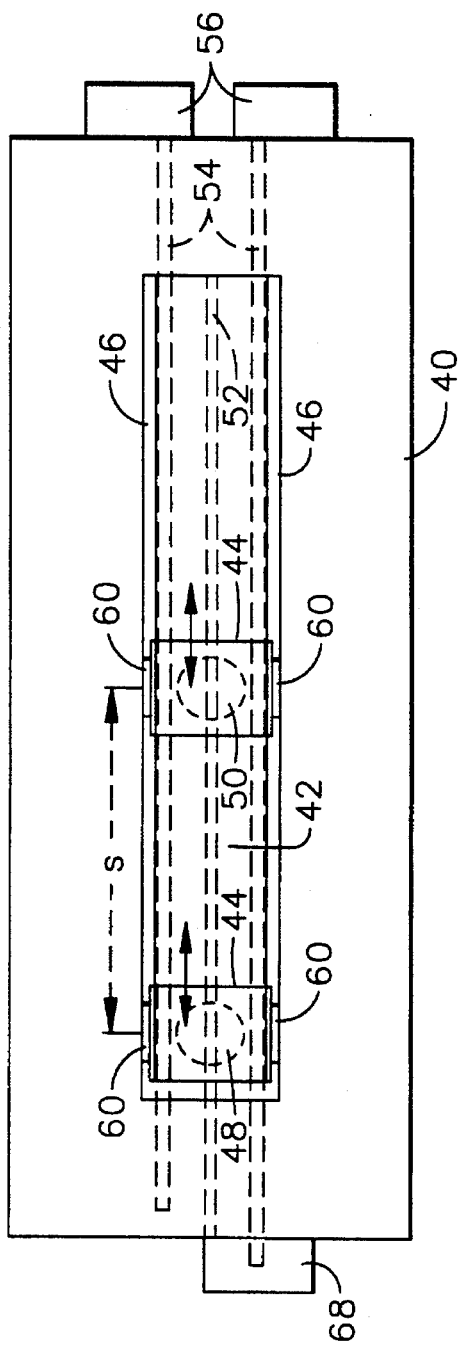
FIGS. 6A and 6B are schematic top and side views, respectively, of a transducer positioning sled in accordance with a preferred embodiment of the invention.
Figure 6B:
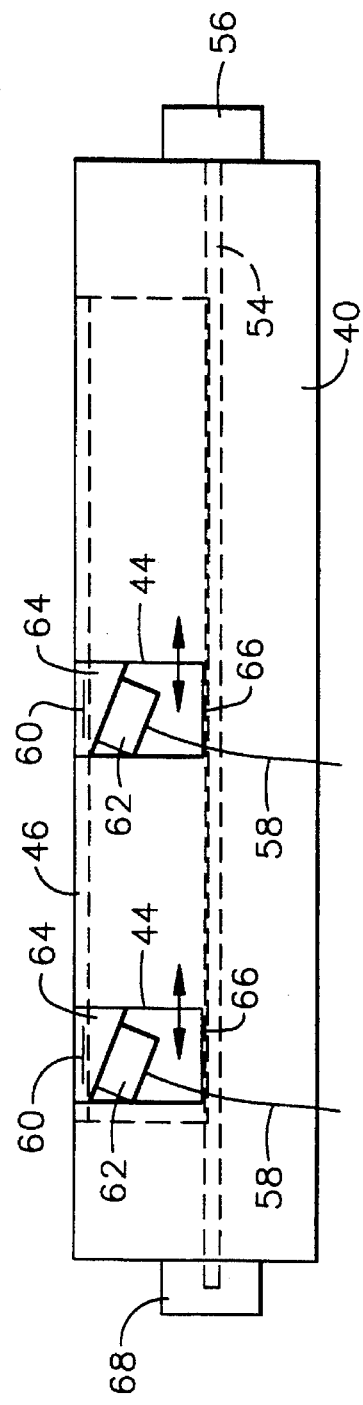

An apparatus for enabling remote adjustment of S and s is shown schematically in FIGS. 6A and 6B. A movable sled 40 contains a slotted guide 42, allowing the transducer dollies 44 to move laterally on tracks 46. Emitter 48 and detector 50 are positioned a distance s apart by two screw drives 54, independently driven by reversible electric motors 56. A slot 52 is provided for electrical leads 58 to access the piezoelectric crystals 62 in contact with the "shoes" 64, which act to provide, or detect, refracted longitudinal waves at the angle $\theta$ in the material being inspected. These transducers are securely affixed to the dollies, which have worm gears 66 in contact with their respective screw drive to move the dollies forward or backward, constrained by the tracks 46 and guides 60. When one or the other of the drive motors is energized by remote means (not shown), the position of the respective dolly can be changed in either direction, with the result that the distance s is continuously variable within the limits of the guide dimension.

By placing the emitter 48 at a known position S, the detector 50 can be located relative to it in order to optimize the acquisition of time-of-flight diffraction data. A shaft encoder 68 is used to accurately determine the emitter location, S, for use in the sizing formula. No position data on the detector location, s, is required, since this parameter does not enter the sizing formula explicitly.

The ultrasonic transducers emitting or receiving pulses must be excited in a specific manner to generate and detect the diffraction signals. The conventional method of excitation uses a short pulse, producing essentially the impulse response of the crystal. However, the presence of the gap places additional restrictions on the signal bandwidth, not encountered in previous pulse diffraction techniques. A preferred mode of excitation will now be disclosed that is compatible with the gap and time-of-flight constraints.

The required resonant frequency $f_0$ has already been discussed above. In addition, the pulse bandwidth BW of the electronics/transducer combination must be sufficiently small so that constructive interference can occur in the gap, thereby allowing gap penetration by the sound wave. On the other hand, the pulsewidth in time, PW, must be short compared to the time-of-flight $\Delta T$ in order to resolve the diffracted pulse(s). These two constraints can be represented as follows:

$$\frac{1}{\Delta T} < BW \ll f_0$$

which can be written as:

$$\frac{c_s}{c_g} \frac{d\sin[\theta]}{S} < \frac{BW}{f_0} \ll 1$$

Figure 7:
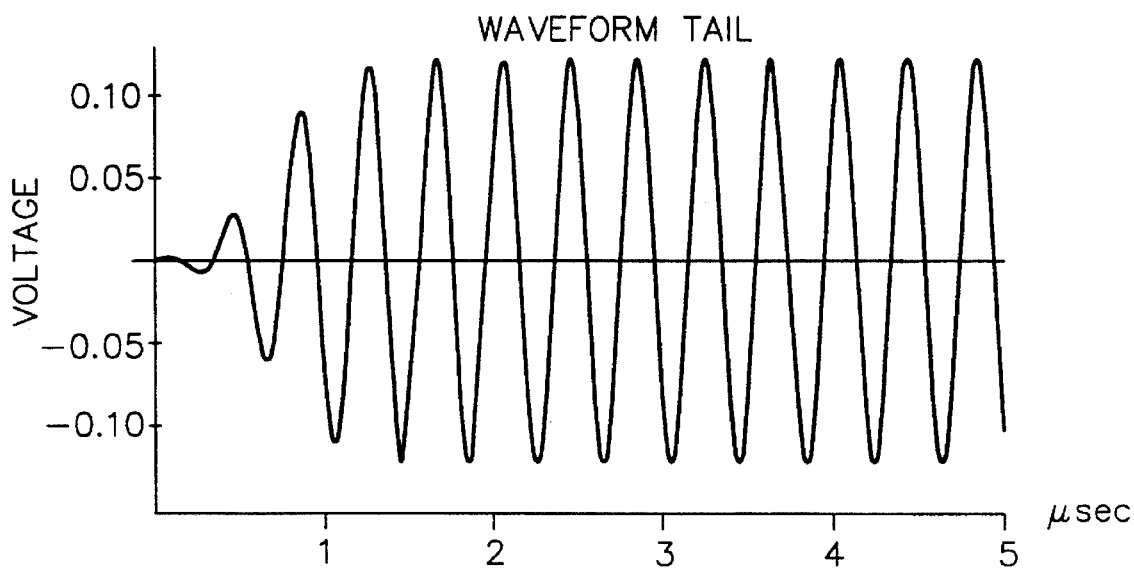
FIG. 7 is a graph depicting the waveform of the response of a 2.25-MHz transducer to 2.519-Mhz excitation.

For narrow gaps and a reasonably large angle of refraction, the left-hand side of this inequality is easily satisfied. The right-hand side is not commonly met by the impulse response of conventional transducers (typically, $BW/f_0 \approx 0.45$). A considerably narrower spectral width can be obtained by driving the transducer at the resonant frequency $f_0$ of the gap. The result is a "tone burst", half of which is shown for a typical case in FIG. 7. The bandwidth of the "pulse" is much smaller than that for the impulse response, so the "tone burst" is a preferred mode of transducer excitation. The scattered pulse has the same form, but reversed in phase and reduced in amplitude.

Figure 8:
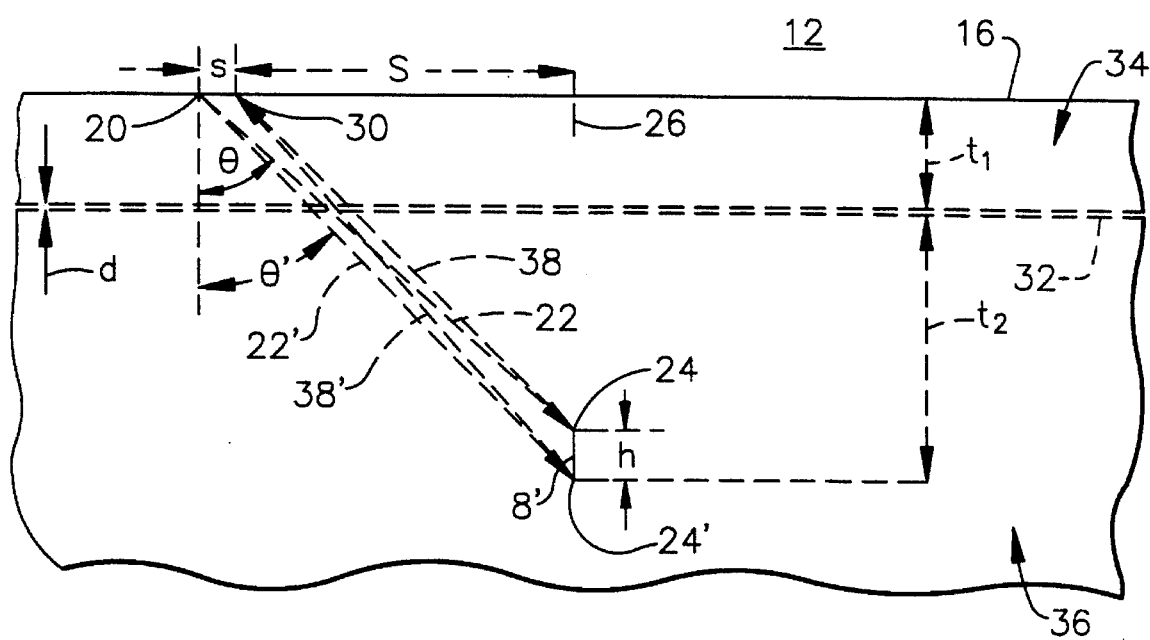
FIG. 8 is a schematic representation of a time-of-flight technique for sizing buried cracks through fluid-filled gaps in accordance with the invention.

The foregoing method is equally applicable to sizing of buried cracks. One difference, however, is that for surface-connected cracks, the emitter is of the focused type, whereas for buried cracks, a defocused emitter should be used. In the latter case, $\Delta T$ will be the difference between the respective times of flight of rays transmitted by the emitter at location 30 at respective angles of incidence $\theta$ and $\theta'$ along paths 22 and 22' (see FIG. 8) and scattered back to the detector at location 30 (located a distance s from the emitter) by the top and bottom edges 24 and 24' respectively of a buried planar crack 8'. Since distance s is of the order of the crack height h, for small cracks (i.e., $h<<t_2$) the resonant frequencies of the gap at the respective points where the incident and scattered rays cross will be substantially equal. For larger cracks, two detectors can be used to detect the rays respectively scattered by the top and bottom crack edges.

I claim:

1. A method for sizing a surface-connected planar crack in a first structure through a fluid-filled gap between said first structure and a second structure, using first and second transducers arrayed on a side of said second structure remote from said gap, comprising the steps of:

emitting ultrasonic energy having a predetermined frequency from said first transducer in an emission mode toward an edge of said planar crack, said gap having a resonant frequency which is substantially equal to said predetermined frequency;

back-scattering a first portion of said emitted ultrasonic energy having said predetermined frequency from said edge of said planar crack toward said first transducer in a detection mode and scattering a second portion of said emitted ultrasonic energy having said predetermined frequency from said edge of said planar crack toward said surface to which said crack is connected;

reflecting said second portion of said emitted ultrasonic energy having said predetermined frequency from said surface to which said crack is connected toward said second transducer in a detection mode;

measuring the time-of-flight from emission to detection of said first portion of said emitted ultrasonic energy having said predetermined frequency;

measuring the time-of-flight from emission to detection of said second portion of said emitted ultrasonic energy having said predetermined frequency;

calculating the difference between the time-of-flight from emission to detection of said first portion of said emitted ultrasonic energy having said predetermined frequency and the time-of-flight from emission to detection of said second portion of said emitted ultrasonic energy having said predetermined frequency; and calculating a distance corresponding to the depth of penetration of said surface-connected planar crack in dependence on said time-of-flight difference.

2. The method as defined in claim 1, wherein said first and second transducers are located on the same side of the plane of said crack.

3. The method as defined in claim 1, wherein said second transducer is located between said crack plane and said first transducer.

4. The method as defined in claim 2, wherein the positions of said first and second transducers can be adjusted by sliding along a track.

5. The method as defined in claim 1, wherein the paths traveled by said first and second portions of said emitted ultrasonic energy having said predetermined frequency substantially intersect at said gap.

6. The method as defined in claim 1, wherein said first and second structures are made of metal and said gap is filled with water or helium.

\* \* \* \* \*